United States Patent
Lindner (10) Patent No.: US 10,702,315 B2
(45) Date of Patent: Jul. 7, 2020

(54) MEDICAL INSTRUMENT FOR PROVISIONALLY FASTENING A POLYAXIAL PEDICLE SCREW

(71) Applicant: Aesculap AG, Tuttlingen (DE)

(72) Inventor: Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 16/097,386

(22) PCT Filed: May 8, 2017

(86) PCT No.: PCT/EP2017/060919
§ 371 (c)(1),
(2) Date: Oct. 29, 2018

(87) PCT Pub. No.: WO2017/194470
PCT Pub. Date: Nov. 16, 2017

(65) Prior Publication Data
US 2019/0142471 A1    May 16, 2019

(30) Foreign Application Priority Data
May 9, 2016   (DE) .................. 10 2016 108 504

(51) Int. Cl.
*A61B 17/70*   (2006.01)
(52) U.S. Cl.
CPC ........ *A61B 17/708* (2013.01); *A61B 17/7037* (2013.01); *A61B 17/7086* (2013.01)
(58) Field of Classification Search
CPC .............. A61B 17/708; A61B 17/7077; A61B 17/7083; A61B 17/7085; A61B 17/7086; A61B 17/7091
See application file for complete search history.

(56) References Cited

U.S. PATENT DOCUMENTS

| 2009/0228054 A1 | 9/2009 | Hoffman et al. |
| 2013/0103094 A1 | 4/2013 | Beale et al. |

(Continued)

FOREIGN PATENT DOCUMENTS

| DE | 102011053295 A1 | 3/2013 |
| EP | 2832308 A1 | 2/2015 |
| WO | 2013034351 A1 | 3/2013 |

OTHER PUBLICATIONS

German Search Report for German Application No. 10 2016 108 504.9, dated Jan. 10, 2017, with English translation—11 pages.

(Continued)

*Primary Examiner* — Julianna N Harvey (57) ABSTRACT

A medical instrument provisionally fastens a polyaxial pedicle screw having a threaded shank. The shank has a shank head, on which a holding sleeve is arranged. A clamping plunger is mounted in the holding sleeve such that the clamping plunger acts on the shank head, such that the holding sleeve can be positionally fixed on the shank head by relative loading of the holding sleeve and the clamping plunger. The instrument has a coupling unit for engaging the holding sleeve and a pressure tappet for applying force to the clamping plunger. The coupling unit and the pressure tappet can be moved relative to each other. The instrument has a sleeve, in which the coupling unit is arranged such that the coupling unit can be moved in the axial direction, decoupled from the holding sleeve in a first position, and fastened to the holding sleeve in a second position.

25 Claims, 9 Drawing Sheets

(56) References Cited

U.S. PATENT DOCUMENTS

| | | | |
|---|---|---|---|
| 2014/0277137 A1* | 9/2014 | Stad | A61B 17/7076 606/246 |
| 2015/0039035 A1 | 2/2015 | Krüger | |
| 2016/0113682 A1 | 4/2016 | Altarac et al. | |
| 2017/0172627 A1 | 6/2017 | Krüger | |

OTHER PUBLICATIONS

International Search Report and Written Opinion for International Application No. PCT/EP2017/060919, dated Aug. 17, 2017—8 pages.

\* cited by examiner

MEDICAL INSTRUMENT FOR PROVISIONALLY FASTENING A POLYAXIAL PEDICLE SCREW

RELATED APPLICATIONS

This application is the United States national phase entry of International Application No. PCT/EP2017/060919, filed May 8, 2017, which claims the benefit of priority of German Application No. 10 2016 108 504.9, filed May 9, 2016. The contents of International Application No. PCT/EP2017/060919 and German Application No. 10 2016 108 504.9 are incorporated by reference herein in their entireties.

FIELD

The present invention relates to a medical instrument for provisionally fastening a polyaxial pedicle screw comprising a threaded shank having a shank head formed proximally thereon, on which shank head a holding sleeve is rotatably and/or pivotally arranged, wherein a clamping plunger is mounted in the holding sleeve in such a way that the clamping plunger acts on the shank head, in such a way that the holding sleeve can be positionally fixed on the shank head by relative loading of the holding sleeve and the clamping plunger, wherein the instrument has a coupling unit for releasably bringing into engagement with the holding sleeve and a pressure tappet, also referred to as an insert pusher, for applying a pressing force to the clamping plunger in the distal direction, wherein the coupling unit and the pressure tappet can be moved relative to each other in an axial direction.

BACKGROUND

Pedicle screws are basically used for dorsal stabilization of the spine by means of transpedicular screwing in the event of fractures, tumors, inflammations, deformities and degenerative instabilities. Pedicle screws are placed in the pedicles of adjacent vertebrae, whereupon an angularly stable connection is created between the axially superimposed pedicle screws and an axially extending longitudinal beam or bridge. The pedicle screws and longitudinal beams form a vertebral stabilization system.

For this purpose, a pedicle screw usually has an axial, shank-like external thread section which is adjoined by a so-called tulip on the screw head side. This tulip forms a U-shaped, longitudinally slotted/tunneled holding sleeve with an internal thread, whereby each of the two radially opposite longitudinal slots defines a slot gap of predetermined gap width. The longitudinal beam/rod is inserted transversely in the parallel extending longitudinal slots and fastened by means of a locking element, for example in the form of a grub screw, threaded nut or set screw, which is screwed into the internal thread.

In general, two basic types of pedicle screws are distinguished, namely uniaxial and polyaxial pedicle screws. In the case of a uniaxial pedicle screw, the external thread section/shank and the tulip/holding sleeve are formed in one piece. A polyaxial pedicle screw, however, has an external thread shank manufactured as a separate component with a mostly spherical or (semi-) spherical screw head, with the holding sleeve/tulip gripping it in a relatively pivotal manner and simultaneously reaching behind the transition area between head and shank. In this way, after lowering the external thread shank into the pedicle channel of a vertebra, the holding sleeve/tulip can be swiveled and/or twisted relative thereto in order to obtain a desired position and orientation substantially independent of the orientation of the shank. The undercut prevents the holding sleeve/tulip from being removed from the shank head. Next, the holding sleeve/tulip is positionally fixed on the screw head by means of the locking element/set screw with an intermediate web (single-screw principle) or by means of an additional screw/ screw nut (multiple-screw principle).

Pedicle screws are inserted by a surgeon into the pedicle canal of a vertebra or anchored by screwing. In doing so, the surgeon aligns the screws based on the orientation of the pedicle canal. When the screws are set, the aforementioned longitudinal beam or bar having the correct length is selected and, if necessary, adapted in its longitudinal curvature to the pedicle screws and their respective positions. The longitudinal beam is to be placed in the tulips of the pedicle screws.

The fact that the holding sleeve of a polyaxial pedicle screw is movably supported relative to the threaded shank makes it easier for the surgeon to insert the longitudinal beam laterally into the holding sleeve. If the surgeon is satisfied with the fit of the longitudinal beam and the holding sleeve, he locks the pedicle screw by means of the locking element, preferably the grub screw (in principle also called a set screw of any configuration). In the case of the above-mentioned single-screw principle, the polyaxial locking (positional fixation of the holding sleeve with respect to the shank) and the longitudinal beam clamping are realized in a single assembly step during tightening the one set screw.

Due to the mobility (joint) between the screw shank and the holding sleeve during the implantation process, it is generally not possible with polyaxial screws to transfer forces from the holding sleeve into the vertebra in order to be able to manipulate it, for example. However, this is particularly necessary for repositioning maneuvers in the case of fractures or spondylolistheses and partly for compressions or distractions. Therefore, uniaxial pedicle screws are used for this purpose, in which the holding sleeve is rigid with respect to the screw shank. However, these uniaxial pedicle screws have the disadvantage that it is difficult to insert the longitudinal beam laterally into the tulip/holding sleeve of several uniaxial pedicle screws.

With many pedicle screws as described above, the fixing means/locking elements (screws) are essentially self-locking to avoid the risk of unintentional loosening of the longitudinal beams from the pedicle screws after implantation. In addition, the fixation forces between the pedicle screw and longitudinal beam are considerable, as the entire system must withstand high loads without the set positional relationship between the threaded shank, holding sleeve and longitudinal beam being allowed to change. This means that the clamping forces between the shank head and the holding sleeve are also very high, so that the frictional connection forming between them is often not released even when the fixing means is released. However, these necessities also cause problems during the implantation process.

As long as the holding sleeve is not fastened relative to the shank head, e.g. firmly connected to the shank head by a frictional connection, no adjustment force can be transmitted to the vertebra by it. In the case of a polyaxial pedicle screw according to the single-screw principle, a longitudinal beam would first have to be inserted and then the locking element, preferably the grub screw, tightened in order to finally be able to apply an adjusting force to the vertebra. However, this would not make technical sense.

Once an operator has tightened the locking element/set screw with force and a subsequent adjustment of the vertebral position may be necessary, the positional relationship thus determined cannot be changed again, or only with great effort. In other words, the surgeon would have to loosen the grub screw(s) tightened with great force against their self-locking effect without loosening or even breaking out the external thread section which is already anchored in the vertebra. Even if the grub screw can be loosened without any problems, a self-locking frictional connection may have developed between the shank head and the holding sleeve. Even if the grub screw is loosened, this frictional connection could only be released with considerable force (knocks on the holding sleeve, etc.). Furthermore, subsequent loosening of the locking element may impair its self-locking effect, so that the functionality of the pedicle screw is no longer guaranteed.

A pedicle screw is known from WO 2013/034351 A1 in which the polyaxiality can be provisionally fixed so that the polyaxiality and the web/longitudinal beam can be locked independently at least temporarily, i.e. only the polyaxiality is fixed without the web being fixed. This publication also discloses a medical device or auxiliary means for provisionally fixing the polyaxiality of a pedicle screw. The pedicle screw essentially consists of a screw shank with a shank head, which is surrounded by a holding sleeve. This holding sleeve supports a plunger that can be pretensioned against the shank head by a locking element. The instrument has a first component in the form of a pressure tappet in order to get into pressing engagement with points of attack provided directly on the plunger. It also has a second component in the form of a sleeve-shaped traction component which is movable relative to the first component and has a latching means which can be brought into pulling engagement with the holding sleeve. The disadvantage of this instrument is that the traction component must be expanded in the area of the pedicle screw's holding sleeve in order to uncouple the traction component. Under certain circumstances, however, this is hardly possible, as bony structures may stand in the way. In addition, the possibility of accidental disconnection of the pedicle screw's holding sleeve cannot be reliably excluded with this instrument.

From US 2014/0277137 A1, a medical instrument is known for provisionally fixing the polyaxiality of a polyaxial pedicle screw, in which an outer component is designed to come into engagement with a holding sleeve of the polyaxial pedicle screw. An inner component received in the outer component is movable relative to the outer component in the axial direction so that the inner component can exert a proximal force on a compression element received in a proximal area of the holding sleeve and thus fix the holding sleeve in position. With this instrument, it is a disadvantage that the locking element/set screw cannot be screwed into the dedicated thread of the holding sleeve in the state when temporarily fastened (with Poly-Lock activated). Furthermore, the small undercut of the holding sleeve can only transmit low fixing forces.

At this point it should be pointed out that the term "provisionally fixing or fastening", especially with regard to the invention described below, is not necessarily meant to mean only easy application/clamping of the shank head, but in particular such a locking measure which is used temporarily and whose achievable locking properties such as the clamping force on the shank head, etc. definitely correspond to, at least come close to or even exceed the permanent locking. In other words, the "provisional" locking should be dimensioned such that it can also cause the holding sleeve to jam on the shank head in accordance with the permanent locking element. In this case, it may be possible to subsequently loosen the frictional connection in accordance with the state of the art by applying the appropriate force, but it is possible to readjust the vertebrae before fixing the longitudinal beam. It is therefore desirable to dimension the "provisional" locking in such a way that sufficient adjustment forces can be transferred to the vertebra by means of the polyaxial pedicle screw, whereby the frictional connection achieved between the shank head and the holding sleeve can be released again.

SUMMARY

Based on the above state of the art, the invention is based on the object of creating an instrument for provisionally fixing the polyaxiality of a polyaxial pedicle screw that does not have the above disadvantages. In particular, the instrument should be easy to handle, allow a secure attachment to the holding sleeve, so that an accidental release of the instrument from the pedicle screw is essentially impossible, allow a stable provisional fastening, so that a vertebra can be manipulated, allow a longitudinal beam to be inserted into the holding sleeve with the instrument arranged thereon, and allow a locking element, for example in the form of a set screw or a grub screw, to be inserted into the holding sleeve, especially in the provisionally fixed state. The instrument should have an easy and safe handling and cleaning and should be inexpensive.

According to the present invention, this object is achieved by an instrument that has a sleeve in which the coupling unit is arranged so as to be movable in the axial direction such that the coupling unit can be coupled to or uncoupled from the holding sleeve in a first axial position and is not detachably fastened to the holding sleeve in a second axial position.

Besides the object of establishing a stable connection between the tulip and the instrument, the instrument according to the invention is especially designed and suitable for provisionally fixing the polyaxiality of a polyaxial pedicle screw. It is to be arranged on or detachably fastened to the holding sleeve of the pedicle screw by means of the coupling unit in order to realize a temporary fixation of the pedicle screw, i.e. a fixation that selectively causes or cancels the coupling. In particular, the coupling unit can be brought into engagement with a coupling structure provided for this purpose and with a mating coupling structure correspondingly formed on the holding sleeve. By relative positioning of coupling unit and sleeve, the instrument can be brought into a connectable state, on the one hand, and into a secured or non-detachable or non-disconnectable state on the other. If the instrument is not detachably coupled to the holding sleeve, a compressive force can be exerted via the pressure tappet onto the clamping plunger of the pedicle screw arranged in the holding sleeve, so that the clamping plunger is relatively positioned relative to the holding sleeve or loaded with the compressive force, and the shank head is clamped between the holding sleeve and the clamping plunger and temporarily fixed in position. According to the invention, the coupling unit and the sleeve can be positioned in a first axial position relative to each other. In said axial position, at least decoupling the coupling unit from the holding sleeve, preferably decoupling from and coupling to the holding sleeve of the pedicle screw is possible. In the second axial position between coupling unit and sleeve, it is not possible to release the coupling unit from the holding sleeve of the pedicle screw and can be prevented by a suitable interaction between sleeve and coupling unit. It can therefore be said that the sleeve represents a safety element which, on the one hand, releases the coupling unit for decoupling or coupling (in the first axial position) and locks it against decoupling (in the second axial position).

Advantageous embodiments of the invention are explained in more detail below.

One embodiment of the invention is characterized in that the coupling unit comprises a radially inwardly projecting detent structure in a distal end region for coupling engagement with a mating detent structure of the holding sleeve provided therefor. In this case, the mating detent structure is preferably formed on the radially outer side of the holding sleeve, so that the receiving space for a longitudinal beam formed inside the holding sleeve as well as the internal thread usually provided inside the holding sleeve for screwing in a set screw are accessible even when the instrument is coupled. This offers the advantage that the longitudinal beam and/or set screw can be manipulated and handled even when the polyaxiality of the pedicle screw is temporarily fixed. The mating detent structure on the holding sleeve can be designed in particular in the form of a stop that is set back radially toward the screw axis, so that the mount is slim and has no sharp-edged protruding parts when the instrument has been removed.

Alternatively or additionally, the detent structure of the coupling unit can be positioned relative to the sleeve in the radial direction, in particular due to elastic deformation of the coupling unit in the radial direction. In this way, the detent structure can take up a first radial position in which it engages in the mating detent structure on the holding sleeve and fixes the instrument thereon and couples it to it. It can also take up a second radial position in which the detent structure is out of engagement with the mating detent structure and decoupling or coupling can take place.

It is particularly advantageous if the coupling unit has at least one coupling arm extending in the axial direction, the distal end region of which can be positioned in the radial direction, in particular due to elastic deformation in the radial direction. Such a coupling arm is advantageously slim, so that it does not require much installation space inside the sleeve. Furthermore, such an arm can have high flexibility or elasticity in the radial and/or tangential direction, with high rigidity in the axial direction. According to one embodiment, the coupling unit may have a plurality of coupling arms. In particular, these can be tangentially spaced from each other and symmetrically designed or arranged relative to one another. For example, the coupling unit may have two coupling arms opposite each other with respect to the axial direction or longitudinal axis, which are tangentially spaced apart by 180° in each case. Similarly, the coupling unit may have three or four coupling arms. A particular advantage of the embodiment with two coupling arms is that there is sufficient space between them, which can be used to feed through the longitudinal beam, the set screw and/or other units such as the pressure tappet or a rod pusher to press the longitudinal beam into the holding sleeve.

The coupling arm or coupling unit can be guided so as to be movable in the axial direction, especially in the sleeve. For this purpose, for example, a guiding groove or guiding shoulder may be formed in the sleeve with which the coupling arm or coupling unit is in a guided contact and is guided in this way.

Preferably, the transition from the coupling arm to the detent structure is formed such that the radially outer side of the detent structure projects radially outwards with respect to the radially outer side of the respective coupling arm.

One embodiment of the invention is characterized in that, in the second axial position in which the coupling unit is not detachably fastened to the holding sleeve, the distal end region of the coupling unit bears against the sleeve in the radial direction. In this case, the sleeve forms an outer border or support for the distal end region, which thus can no longer deform or move in the radial direction. Loosening of the coupling structure from the mating coupling structure of the holding sleeve is prevented by the contact with the sleeve. According to one embodiment, the sleeve and the distal end region of the coupling unit can be designed and matched to one another in such a way that the sleeve, during a relative movement from the first axial position to the second axial position, causes a movement of the detent structure which brings it into engagement with the mating detent structure. For example, the coupling unit and/or the sleeve can be provided with a ramp surface or guiding contour which in the event of an axial positioning from the first to the second axial position causes a feed movement of the coupling structure in the radial direction. In this way, the surgeon can be given feedback as to whether the coupling unit is coupled to the holding sleeve and whether this coupling is secured. If the sleeve cannot be brought into the second axial position, there is no coupling. It is particularly advantageous if the holding sleeve of the pedicle screw has an outside ramp or projection structure in the axial direction for the coupling structure of the coupling unit when viewed in the radial direction. This allows the coupling structure to be easily inserted and latched in place in the mating coupling structure of the holding sleeve in one axial direction for engagement, while the ramp or projection structure prevents it from simply loosening in the opposite axial direction. For example, the surgeon can easily pick up and couple a pedicle screw to the coupling unit through the ramp structure, whereas the separating process requires a specific mechanism.

One embodiment of the invention is characterized in that the coupling unit and the sleeve are in engagement with one another via a thread and can be axially positioned by mutual rotation. In particular, a threaded sleeve or threaded nut may be provided which is to be engaged or is engaged with a counter thread formed on the coupling unit. The threaded sleeve/threaded nut is coupled to the sleeve in a rotatable but axially fixed manner. By screwing the threaded sleeve/threaded nut in the mating thread, the sleeve and the coupling unit are positioned axially relative to each other. In particular, the threaded sleeve/nut may have an internal thread and the coupling unit may have an external thread as a counter thread. It is in the scope of the invention if the sleeve is provided with the counter thread and the coupling unit is rotatably coupled to the threaded sleeve/thread nut, but axially fastened relative thereto. The embodiment described above provides a very precise and patient-friendly adjustment possibility which requires only low actuating forces. In particular, the thread may be provided with a self-locking feature or formed so as to be self-locking by itself, so that an accidental positioning of coupling unit and sleeve in the second axial position can be reliably prevented.

According to one embodiment of the invention, it is provided that the sleeve has its distal end provided with a mount for a section of the holding sleeve. This can be in the form of a groove, a projection or an undercut, for example, and in particular be formed in the circumferential direction either in sections or continuously. In particular, the mount may be formed on a distal end face which may be oriented essentially transverse to the longitudinal axis. The section of the holding sleeve and the mount for it are preferably designed and set up in such a way that they can be coupled to one another via positive locking or frictional connection, if necessary.

A further embodiment of the invention is characterized in that the sleeve has a central passage in the axial direction which has a substantially oval or elliptical cross-sectional shape transverse to the axial direction, for receiving an eccentric so as to be able to rotate about the axial direction for expanding the sleeve and/or the coupling unit.

It is of particular advantage if the coupling unit is provided with a central passage in the axial direction in which the pressure tappet is arranged so as to be able to be positioned axially. This ensures direct and safe action on the clamping plunger mounted in the holding sleeve. In particular, the pressure tappet may have a substantially hollow cylindrical design and comprise a central passage in the axial direction. It may also have an axially extending window or openings that provide access to the internal thread formed in the holding sleeve for screwing in the set screw even when the instrument is attached and especially when the polyaxiality is provisionally fixed, as well as the possibility of inserting a rod pusher or other instruments in the axial direction from the proximal side of the instrument.

According to one embodiment of the invention, the pressure tappet has the proximal end provided with a substantially cylindrical, in particular hollow cylindrical base which is rotatable about the axial axis but coupled to the pressure tappet in an axially fixed manner. This base is in engagement with the coupling unit and serves for axially positioning the pressure tappet in the coupling unit and thus relative to the holding sleeve of the pedicle screw. It is preferred that the corresponding external thread is provided at the base, via which the pressure tappet and the coupling unit are in engagement with each other via an internal thread of the coupling unit and can be axially positioned by mutually turning them. The base of the pressure tappet preferably has a structure on the inner side, especially in the form of a surrounding hub, which is suitable for applying a torque to the base. This allows the axial positioning of the pressure tappet to be carried out using a tool. On the upper side of the proximal end of the base, a structure is provided preferably in surrounding fashion, in particular a knurled/serrated structure, which is suitable for positively engaging in a mating structure and thus also transmitting a torque. It is also advantageous if an area of the side wall of the pressure tappet, preferably along the axial direction, has an opening for easy access to the interior.

Another embodiment of the invention is characterized in that the instrument has a rod pusher for pressing a rod/longitudinal beam/spinal rod to be fastened in the holding sleeve of the pedicle screw in the distal direction. The rod pusher can be axially positioned in the axial direction, especially in the central passage of the pressure tappet.

Another embodiment of the invention is characterized in that the rod pusher also has a central passage in the axial direction. This passage may be used to insert a set screw through the instrument into the holding sleeve, especially when the pedicle screw is temporarily fastened. Furthermore, a screw-driving tool can be passed for screwing action on the pedicle screw and/or the set screw.

In one embodiment of the invention, the rod pusher at its proximal end has a screw head which is freely rotatable but coupled to the rod pusher in an axially fixed manner and is formed to be essentially cylindrical, in particular hollow-cylindrical. This screw head is used to adjust the axial positioning of the rod pusher in the coupling unit and thus the axial positioning relative to the rod. The distal end of the screw head is preferably provided with an external thread. This external thread meshes with the correspondingly provided internal thread of the coupling unit, with the axial position of the rod pusher being able to be adjusted by turning. The underside of the distal end of the screw head is preferably provided with a structure, in particular a knurled structure, which is suitable for engaging in a second structure, in particular the knurled structure of the pressure tappet, and thus transmitting torque in a form-fitting manner. Preferably, a scale is provided on the radial outside of the screw head, from which the surgeon can read off an axial positioning or screw depth. It is particularly advantageous if a structure is provided at the proximal end of the screw head, especially on the inner side, which is suitable for transmitting a torque. A tool can be inserted into this structure with a positive fit and thus the screw head can be screwed into the internal thread of the coupling unit and positioned axially via an appropriate external thread. An instrument, in particular a screw-driving tool, can be inserted through a central passage in the axial direction. Furthermore, a structure is provided preferably on the inner side of the screw head near the proximal end, in particular an internal thread via which a screw-driving tool can be screwed in, and a geometric boundary is provided near the distal end, whereby after insertion of an instrument, in particular a screw-driving tool, this is arranged so as to be movable in the axial direction between two positions within the rod pusher.

In one embodiment of the invention, the medical instrument also includes a screw-driving tool. This screw-driving tool has the distal end provided with a structure/entraining profile which is suitable for applying a form-fitting torque or screw actuation in particular to the set screw and/or the pedicle screw. Furthermore, the screw-driving tool has the proximal end provided with a structure/receiving profile which is suitable for receiving a torque in a form-fitting manner, in particular through a handle. Seen in the axial direction, the screw-driving tool is provided with a structure in a central area, preferably with an external thread, which is suitable for engaging in the (mating) structure of the screw head described above, in particular the internal thread, whereby the screw-driving tool can be secured, for example, against accidentally falling out.

In a further embodiment of the invention, the medical instrument has a rod pusher for pressing a rod or longitudinal beam to be fastened in the holding sleeve of the pedicle screw in the distal direction, the pressure tappet and the rod pusher being designed as a one-piece pressing unit. Therefore, the pressing unit in its embodiments preferably still has the features of pressure tappet and rod pusher described above, in particular a guide protrusion for guiding the pressing unit in the sleeve, a central passage in the axial direction, a screw head and support pins at the distal end.

The axial positioning of the one-piece pressing unit in the sleeve provides a provisional fixing of the polyaxiality of the pedicle screw as well as a positional fixation of the rod. A screw-driving tool for screwing action on the pedicle screw and/or set screw can be passed together with a set screw through a central passage of the pressing unit from the proximal end of the instrument. The one-piece design of the pressure tappet and rod pusher allows, among other things, the central passage to be designed larger.

In a preferred embodiment, the medical instrument is distinguished in that the detent structure engages in a mating detent structure formed by the sleeve in such a way that a tensile force, i.e. a force in the proximal direction, can be transmitted from the coupling unit to the sleeve when actuated accordingly by an operator. This enables the instrument to make corrections in the fixation of the pedicle screw, which facilitates an efficient attachment of the screw in the patient.

It is particularly advantageous here if the mating detent structure has at least one surface which extends at least partially in the horizontal direction and relative to which the detent structure can be arranged distally in order to transmit the tensile force in a form-fitting manner. That surface preferably extends at least partially in the plane relative to which the longitudinal axis of the instrument is orthogonal. This enables the detent structure to contact a stop in the mating detent structure during a traction movement, i.e. during a movement in the distal direction, which guarantees reliable force transmission.

If the mating detent structure has a bulbous/partially circular/drop-shaped form in its distal end region, i.e. at the section facing the shank, the form fit for the transmission of tensile force can be realized efficiently. This geometry refers to the shape of the mating detent structure in a frontal view. Moreover, or alternatively, it is advantageous if the mating detent structure has two opposite, circumferentially projecting indentations in the form of an undercut so that the mating detent structure takes on a cross-like shape.

In summary, it can be stated that the invention provides an instrument, also known as a downtube, with a locking option for polyaxial clamping and an implant locking function.

BRIEF DESCRIPTION OF THE DRAWING FIGURES

Further features and advantages of the present invention will be apparent from the following exemplary and non-restrictive description of the invention on the basis of Figures. These are only schematic in nature and only help to understand the invention.

FIG. 1 to FIG. 16 show a medical instrument according to a first embodiment of the present invention. FIG. 17 to FIG. 20 show an instrument according to a second embodiment of the present invention.

DETAILED DESCRIPTION

Figure 1:
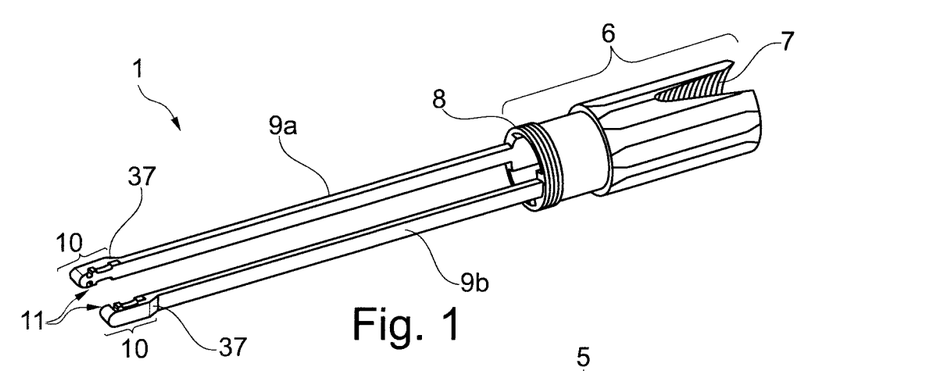
FIG. 1 is a perspective view of a coupling element of an instrument according to the invention.

A medical instrument of a first embodiment according to the invention comprises a coupling unit 1 (which can also be referred to as coupling element 1), a sleeve 2, a pressure tappet 3, a rod pusher 4 and an adjusting nut 5. The medical instrument 1 according to the invention may further comprise a screw-driving tool 45. FIG. 1 shows the coupling unit 1 or coupling element 1, FIG. 2 the sleeve 2 with the adjusting nut 5, which is rotatable but fastened axially in at least one direction, FIG. 3 the pressure tappet 3 and FIG. 4 the rod pusher 4, each in a perspective view. In FIGS. 1 to 7 and 16 and 17, the left side of the Figure represents the distal side and the right side of the Figure represents the proximal side of the element or instrument shown. The longitudinal axis or axial direction in the sense of the present description extends from the distal side to the proximal side and vice versa.

The coupling element 1 has a substantially hollow cylindrical proximal base 6 provided with an internal thread 7, and an external thread 8 at its distal end region. From the base 6, two coupling arms 9a, 9b extend in the distal direction. The coupling arms 9a, 9b are parallel to each other and are diametrically opposed, i.e. they enclose an angle of 180° between them on each side. At the distal end section of each coupling arm 9a, 9b a coupling structure 10 is formed in each case. On the radially outer side, the transition from the coupling arm 9a, 9b to the coupling structure 10 is formed with an inclined surface 37 in each case, and the radially outer side of the coupling structure 10 projects radially outwards with respect to the radially outer side of the respective coupling arm 9a, 9b. On the radially inner side of each coupling structure 10, a detent structure 11 is formed in each case for engagement with a corresponding mating detent structure 12 which is formed on a holding sleeve 13 of a polyaxial pedicle screw 14 (see, for example, FIG. 6, 9 or 10). The detent structure 11 and the mating detent structure 12 are each designed in such a way that they latch in place both in axial direction and tangential direction (circumferentially).

Figure 2:
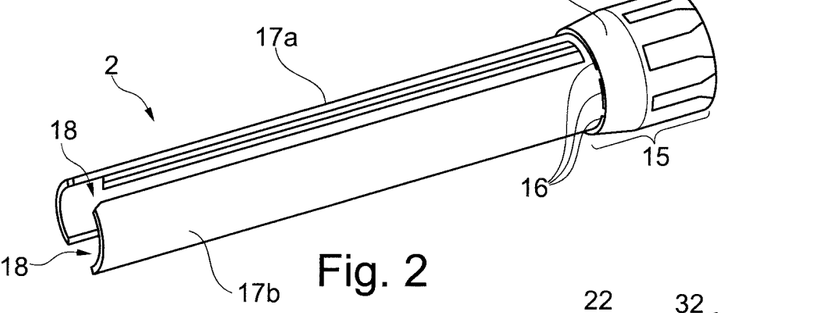
FIG. 2 is a perspective view of a sleeve of an instrument according to the invention.
Figure 8:
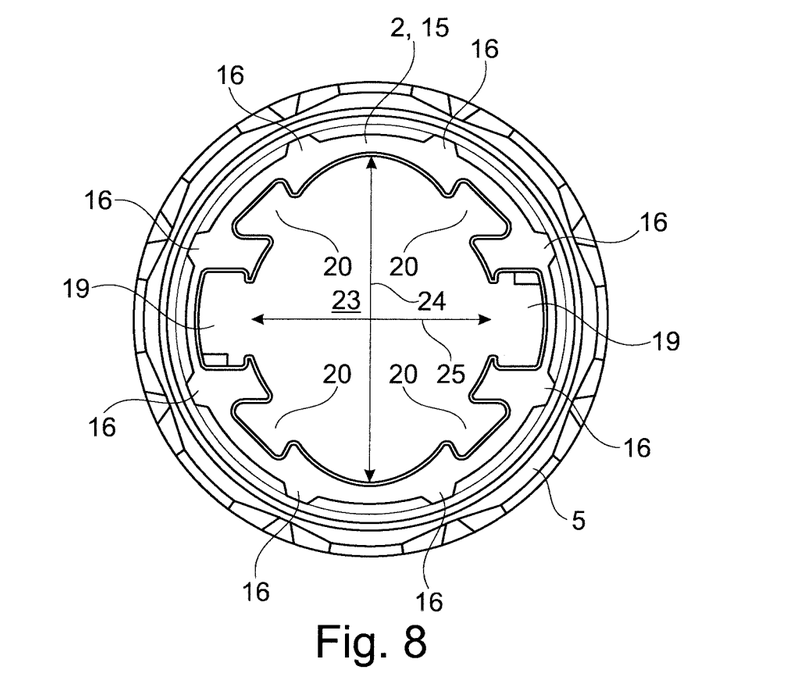
FIG. 8 is a cross-section through the sleeve of FIGS. 5 and 6.
Figure 9:
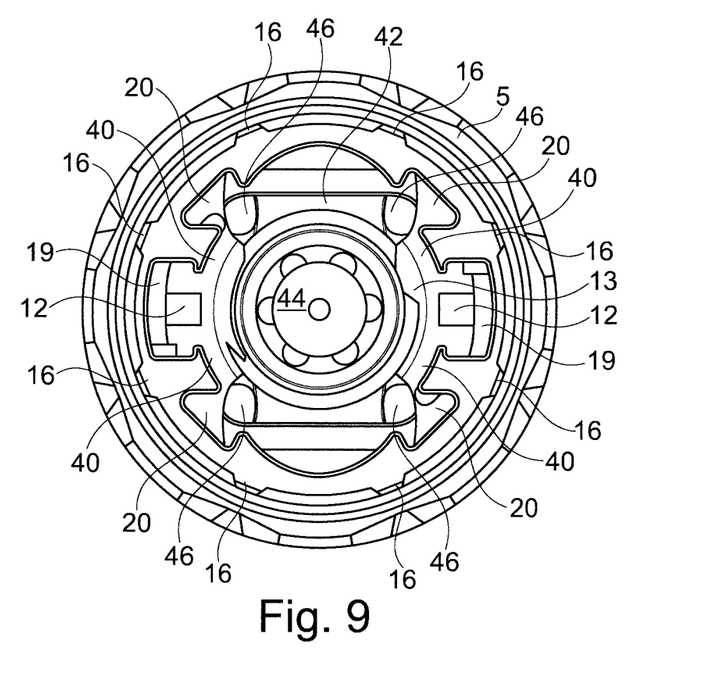
FIG. 9 is another cross-section through the sleeve of FIGS. 5 and 6 with the pedicle screw comprising a pressure tappet and a set screw.

The sleeve 2 also has a proximal base 15 whose distal end region is formed with a plurality of shoulders 16 or stops 16. These serve as a bearing region for the adjusting nut 5, so that the sleeve 2 cannot move out of the adjusting nut 5 in the distal direction or the adjusting nut 5 cannot be removed proximally from the sleeve 2. Distal to the base 15, the sleeve comprises two partially cylindrical sleeve arms 17a, 17b arranged diametrically opposite each other. Each of the sleeve arms 17a, 17b extends in a circumferential direction by approx. 90°, so that two diametrically opposite windows 18 or spaces 18 are formed between them. FIGS. 8 and 9 show the sleeve 2 in a cross section transverse to the axial direction in the area of its proximal base 15. The shoulders/stops 16 protruding radially outwards are clearly visible. Radially inwards, the sleeve 2 is provided with two opposing guiding grooves 19 for the coupling arms 9a and 9b, respectively. A guiding groove 20 is formed on both sides of each guiding groove 19, i.e. there is a total of four guiding grooves 20 for the guided reception of a respective guide protrusion 22 of the pressure tappet 3. FIGS. 8 and 9 also clearly show that the sleeve 2 is penetrated by a continuous passage 23, which is formed in the axial direction. This passage 23 has an oval or elliptical cross-section. Its large half axis 24 extends from a window 18 to the opposite window 18. Its small half axis 25 extends transverse to the large half axis 24, for example from a sleeve arm 17a to the opposite sleeve arm 17b. This design of passage 23 serves to accommodate an eccentric instrument (not shown in the Figures) and allows for the cooperation with it, by means of which the two opposite sleeve arms 17a, 17b can be spread by turning it about the longitudinal axis (in the context of a detachment of the instrument from a holding sleeve 13 of a pedicle screw).

Figures 3, 4:
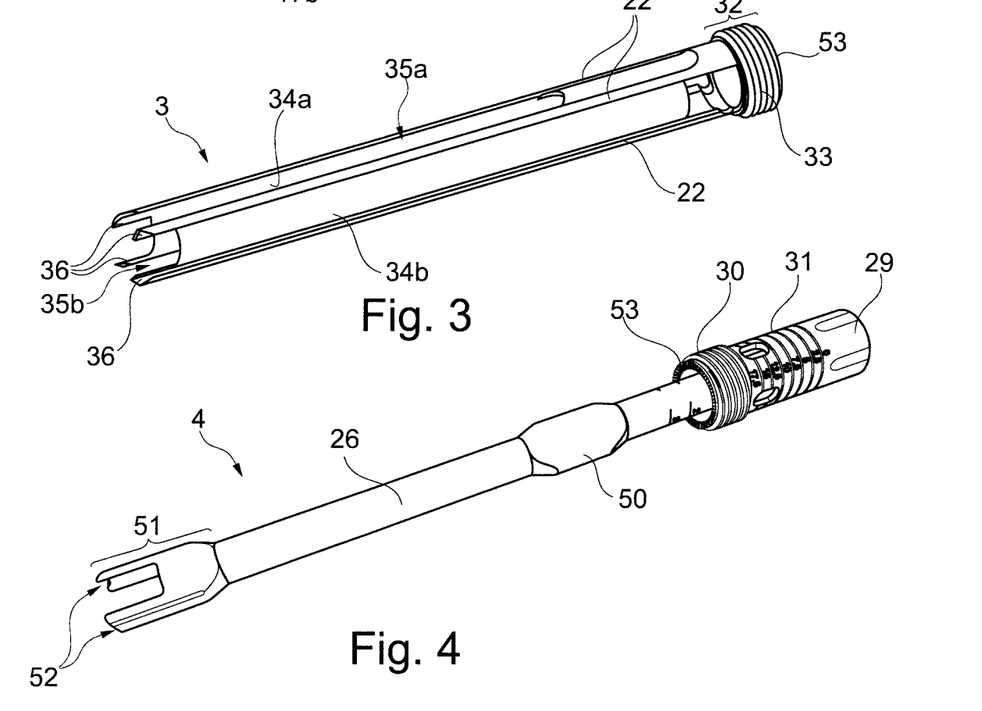
FIG. 3 is a perspective view of a pressure tappet of an instrument according to the invention.
FIG. 4 is a perspective view of a rod pusher of an instrument according to the invention.

The pressure tappet 3 is essentially designed in the form of a hollow cylinder. It has a proximal base 32, which is coupled rotatably with the pressure tappet 3 but is axially fastened thereto, and which has an external thread 33. Distal to the base 32, the pressure tappet 3 has two partially cylindrical plunger arms 34a, 34b arranged diametrically opposite each other. Each plunger arm 34a, 34b extends in the circumferential direction by approx. 90°, so that two diametrically opposite windows 35a, 35b or spaces 35a, 35b are formed between them. The window 35a is larger than the window 35b, allowing better access to the interior of the pressure tappet 3. The distal end of the pressure tappet 3 is provided with four support pins 36 projecting in the axial direction. The external thread 33 of the rotatable base 32 is intended and designed for engagement with the internal thread 7 of the coupling element 1. By screwing the pressure tappet 3 into or out of the coupling element 1, their axial positioning relative to each other takes place, and thus a corresponding axial positioning of the support pins 36 relative to the coupling structure 10. The pressure tappet 3 also has the four guide protrusions 22 uniformly spaced over the circumference. These are intended and designed for guided interaction with the guiding grooves 20 of the sleeve 2.

The rod pusher 4, which can be inserted into the central passage of the pressure tappet 3, has a substantially cylindrical rod 26 whose distal section 51 is provided with a rod mount 52. The proximal end of the rod pusher 4 has a screw head 29 which is rotatable relative to the rod pusher 4 but coupled to it in an axially fixed manner and which is provided with an external thread 30 and has a scale 31 by means of which the surgeon can recognize the screw-in depth of the rod pusher 4. The external thread 30 of the screw head 29 is intended and designed for engagement with the internal thread 7 of the coupling element 1. By screwing or unscrewing the rod pusher 4 into or out of coupling element 1, their axial positioning relative to one another takes place, and thus a corresponding axial positioning of the rod mount 52 relative to coupling structure 10. The screw head 29 has a knurled structure 53 on the distal underside, which is suitable for engaging in the knurled structure 53 on the proximal upper side of the base 32 of the pressure tappet 3. An oval shape 50 is formed in a central section which is suitable for guiding the rod pusher 4 in the pressure tappet 3 in the axial direction and limiting the rotational freedom of the cylindrical rod 26 of the rod pusher 4 with respect to the pressure tappet 3. A hub structure is provided on the proximal end of the rod pusher 4 on the inner side of the screw head 29, into which a (not shown) tool can engage positively and transmit a torque. Furthermore, an internal thread is provided on the inner side of the screw head 29 in a central section of the screw head 29 near the proximal end, and a limitation means in the form of a geometric stop is provided near the distal end. The external thread 49 of the screw-driving tool 45 is screwed into this internal thread. According to this, the screw-driving tool 45 is axially movable between the two positions, corresponding to the distance from the internal thread to the limitation means.

Figure 5:
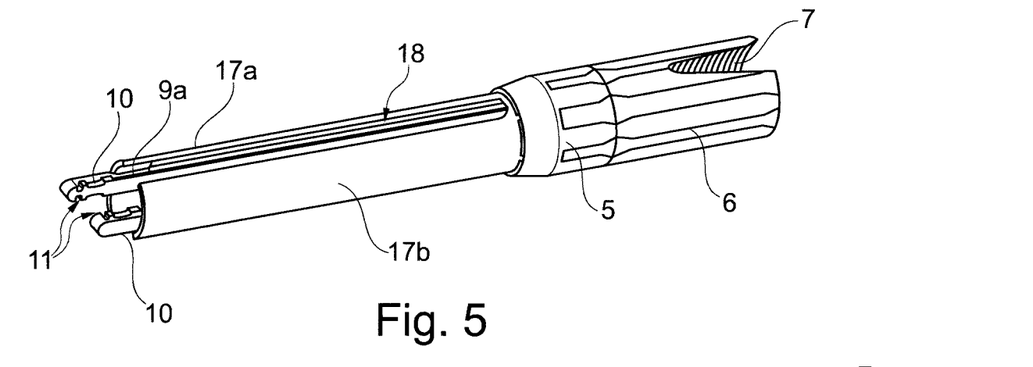
FIG. 5 is a perspective view of a coupling unit and a sleeve plugged together in a first axial position.
Figure 6:
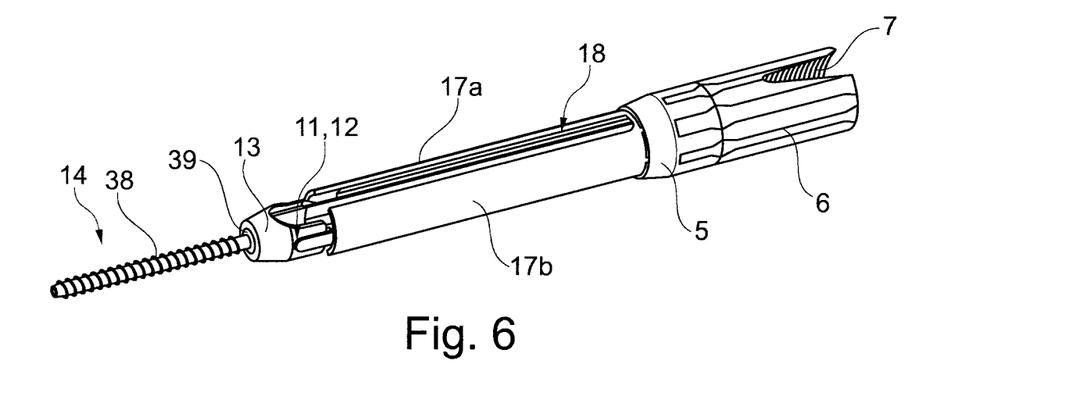
FIG. 6 is a perspective view of the coupling unit and the sleeve of FIG. 5 with a polyaxial pedicle screw in the first axial position.

FIGS. 5 and 6 show the coupling unit 1 and the sleeve 2 plugged together in the first axial position, with FIG. 6 showing a pedicle screw 14 gripped by means of the coupling arms 9a, 9b. FIG. 6 clearly shows a threaded shank 38, at the proximal end of which a shank head 39 is formed, on which in turn the holding sleeve 13 is arranged so as to be able to rotate and/or pivot. In the first axial position shown in FIGS. 5 and 6, the coupling structures 10 of each coupling arm 9a, 9b project out of the sleeve 2 in the axially distal direction and protrude with respect to the distal ends of the sleeve arms 17a, 17b.

Figure 7:
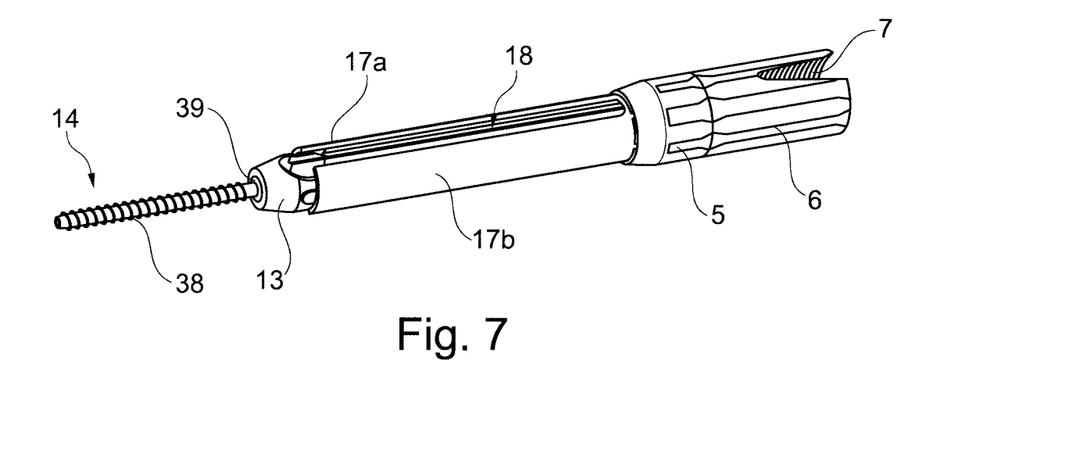
FIG. 7 is a perspective view of the coupling unit and the sleeve of FIGS. 5 and 6 with the polyaxial pedicle screw in the second axial position.
Figure 10:
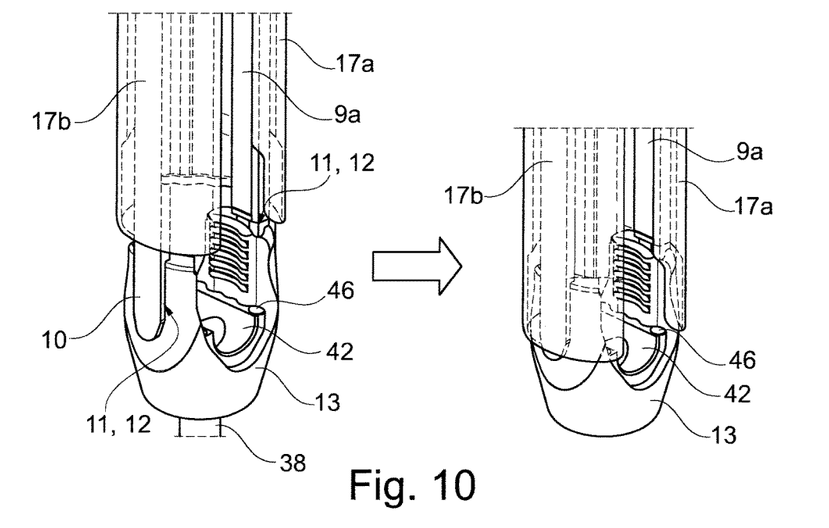
FIG. 10 is a truncated perspective view of the coupling unit and the sleeve of FIGS. 5 and 6 showing the transition from the first axial position to the second axial position.

FIG. 7 shows the coupling unit 1 and the sleeve 2 when plugged together in the second axial position with the coupled pedicle screw 14. By having tightened the adjusting nut 5, the coupling unit 1 is retracted in the axially proximal direction relative to the sleeve 2. As a result, the coupling arms 9a, 9b with the coupling structures 10 and the holding sleeve 13 coupled to them have also been drawn into the sleeve 2. Since the radially outer side in the transition from the coupling arm 9a, 9b to the coupling structure 10 is each formed with an inclined surface 37 and the radially outer side of coupling structure 10 projects radially outwards with respect to the radially outer side of the respective coupling arm 9a, 9b and rests against the inner side of the sleeve arms 17a, 17b, the coupling arms 9a, 9b are pressed radially inwards into engagement with the mating detent structure 12 of the holding sleeve 13 of the pedicle screw 14 during an axial movement from the first axial position to the second axial position by interaction with the sleeve arms 17a, 17b. In the second axial position shown in FIG. 6, it is not possible to release the detent structure 11 of the coupling structures 10 from the respective mating detent structures 12 of the holding sleeve 13 due to contact with the sleeve arms 17a, 17b. FIG. 10 shows the movement from the first axial position (left) to the second axial position (right) in an enlarged view. In this embodiment, it is advantageous that both coupling arms 9a, 9b of the coupling unit 1 have a slight insertion bevel at their radial inner side at the distal end, and the holding sleeve 13 has a corresponding opposite ramp structure on its radial outer side, which facilitates engagement/coupling of the detent structure 11 of the coupling structure 10 to the mating detent structure 12 of the holding sleeve 13.

Figure 11A:
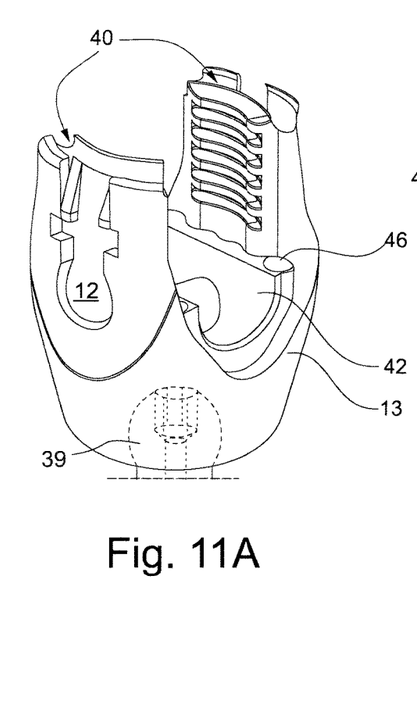
FIG. 11A is an enlarged truncated perspective view of the connection area of the pedicle screw of FIG. 6.
Figure 11B:
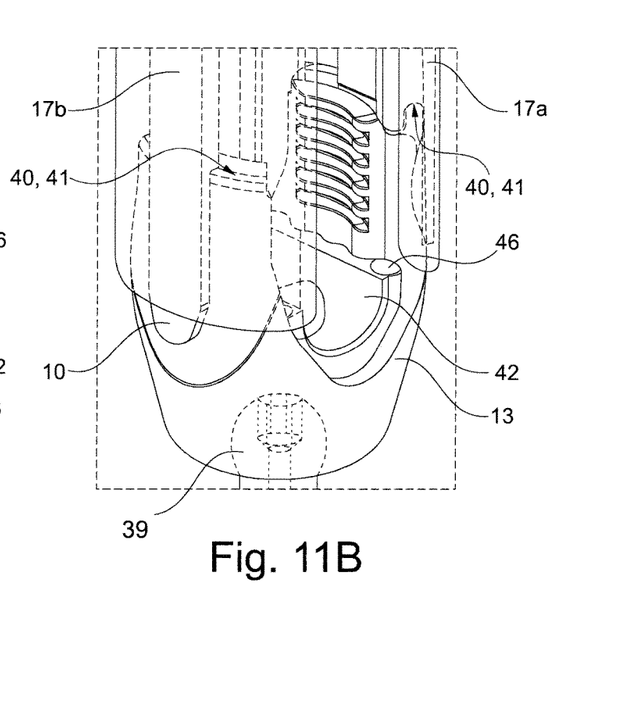
FIG. 11B is an enlarged truncated perspective view of the connection area of the instrument and the pedicle screw of FIGS. 5 and 6.

FIG. 11A shows a section of the pedicle screw 14 with the mating detent structure 12 and the ramp structure of the holding sleeve 13. FIG. 11B clearly shows the engagement of the sleeve aims 17a, 17b with the holding sleeve 13 in detail. A groove 40 or an undercut 40 extending in the circumferential direction is inserted into the proximal end face of the holding sleeve 13. An appropriately designed mating contour 41 or an undercut 41 of the sleeve arms 17a, 17b engages therein, so that the sleeve 2 is connected to the holding sleeve 13 by positive locking via the undercuts 40 and 41.

Figure 12:
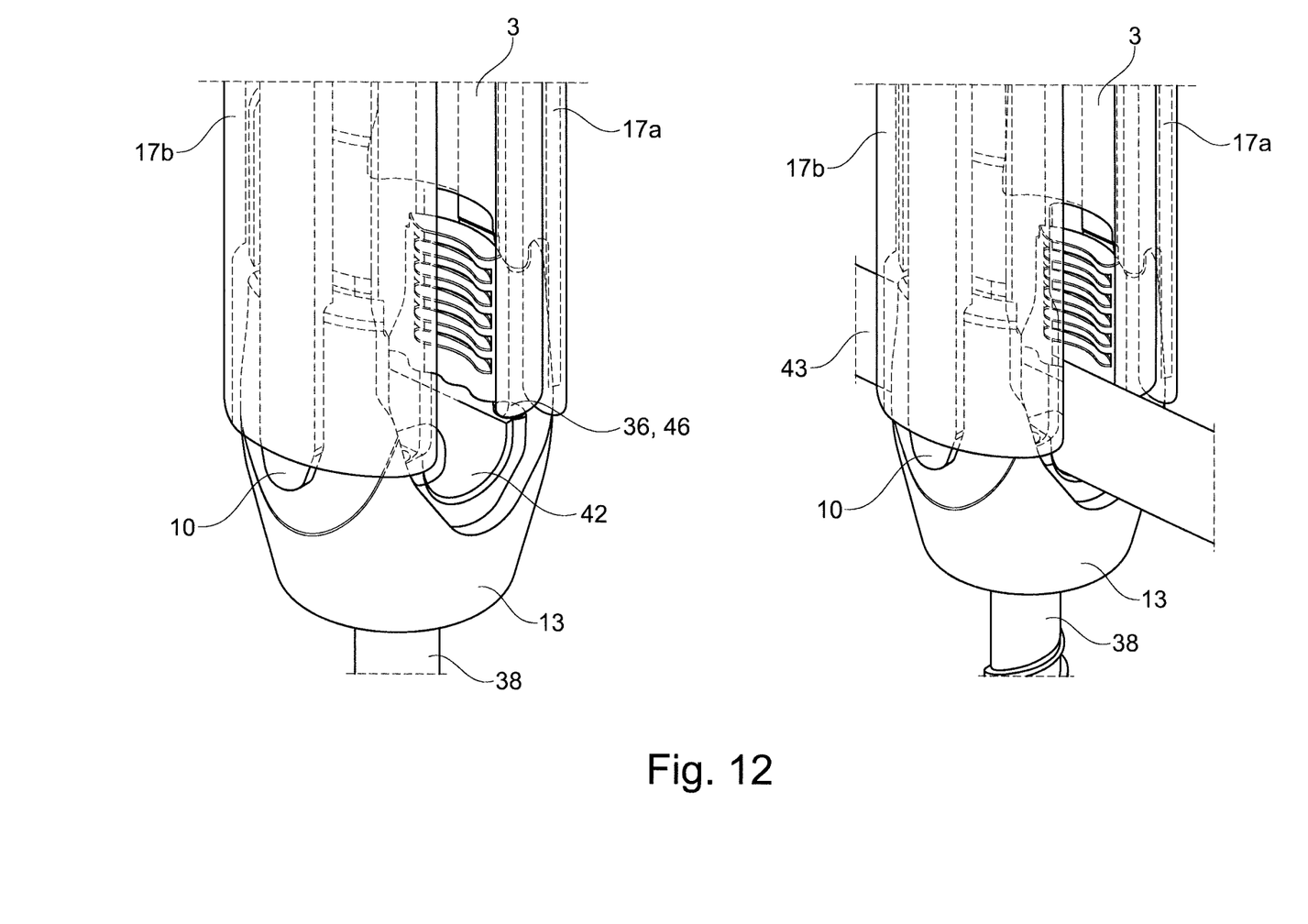
FIG. 12 is an enlarged truncated perspective view of the connection area of the instrument and the pedicle screw of FIGS. 5 and 6 with an inserted pressure tappet with and without a longitudinal beam.

FIG. 12 shows how the instrument works with the pressure tappet 3. In particular, a clamping plunger 42 with four indentations 46 for the interaction and reception of the support pins 36 can be seen, which is mounted in the holding sleeve 13. The clamping plunger 42 is in contact with the shank head 39. In both Figures, the coupling unit 1 and the sleeve 2 are in the second axial position relative to each other, so that the holding sleeve 13 is coupled to the instrument in a secure, axially fixed, non-rotatable and undetachable manner. The pressure tappet 3 is inserted in the passage 23. By screwing the pressure tappet 3 in the internal thread 7 of the coupling unit 1, a corresponding positioning relative to the sleeve 2 and to the coupling unit 1 and thus relative to the coupled holding sleeve 13 of the pedicle screw 14 takes place. This results in a tensioning of the clamping plunger 42 relative to the holding sleeve 13, so that the shank head 39 is clamped between them and the polyaxiality of the pedicle screw 14 is provisionally fastened or blocked.

Figure 13:
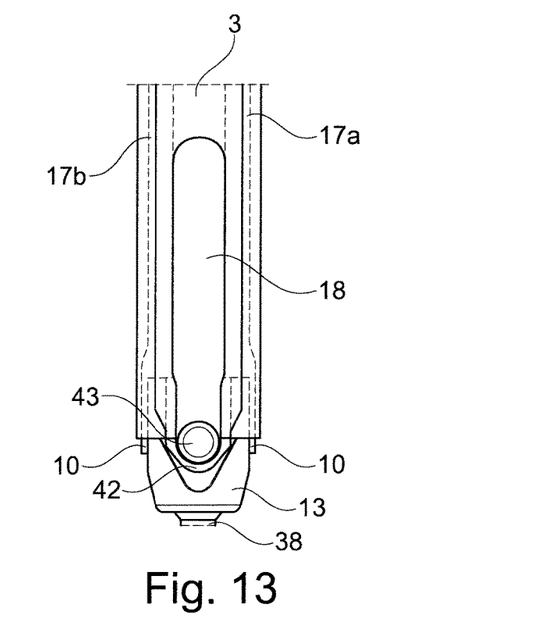
FIG. 13 is an enlarged truncated lateral view of the connection area of the instrument and the pedicle screw of FIGS. 5 and 6 with a pressure tappet inserted.
Figure 14:
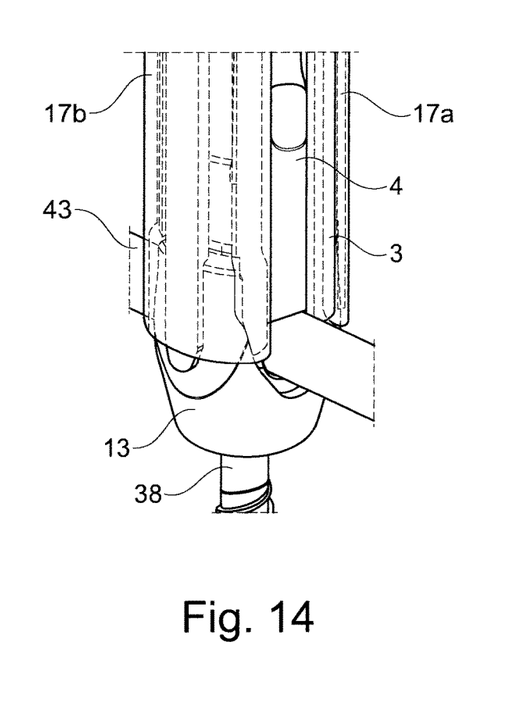
FIG. 14 is an enlarged truncated perspective view of the instrument and the pedicle screw of FIGS. 5 and 6 showing the process of pressing a longitudinal beam by means of the rod pusher into the holding sleeve.

FIG. 12 on the right shows a longitudinal beam 43 accommodated in the holding sleeve 13. FIG. 12 shows that the pressure tappet 3 indeed blocks the polyaxiality of the pedicle screw 14 by contact with the clamping plunger 42, but the longitudinal beam 43 can be positioned relatively freely in the windows 18 and 35a, 35b (see also FIG. 13).

Figure 16:
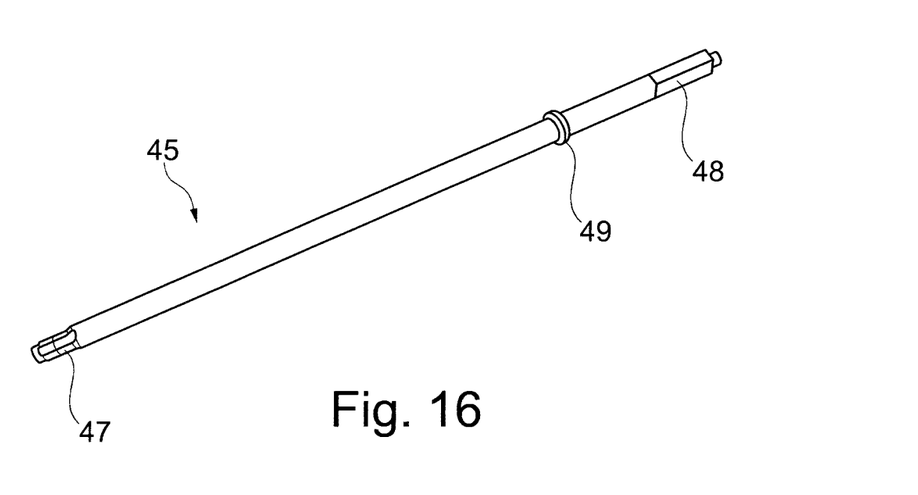
FIG. 16 is a perspective view of a screw-driving tool of an instrument according to the invention.

FIG. 16 shows an embodiment of a substantially cylindrical screw-driving tool 45 comprising a proximal hexagonal attachment profile 48 for being gripped by a handle (not shown) in a form-fitting manner, a distal entraining profile 47 for gripping the set screw 44 in a form-fitting manner, and an external thread 49 in the middle area for screwing it into the internal thread of the rod pusher 4. The entraining profile 47 also has a slotted ring at the distal end, which can be compressed with a certain amount of clearance to secure a set screw 44 with a corresponding radially circumferential groove on the inner side against unintentional release from the screw-driving tool 45.

Figure 15:
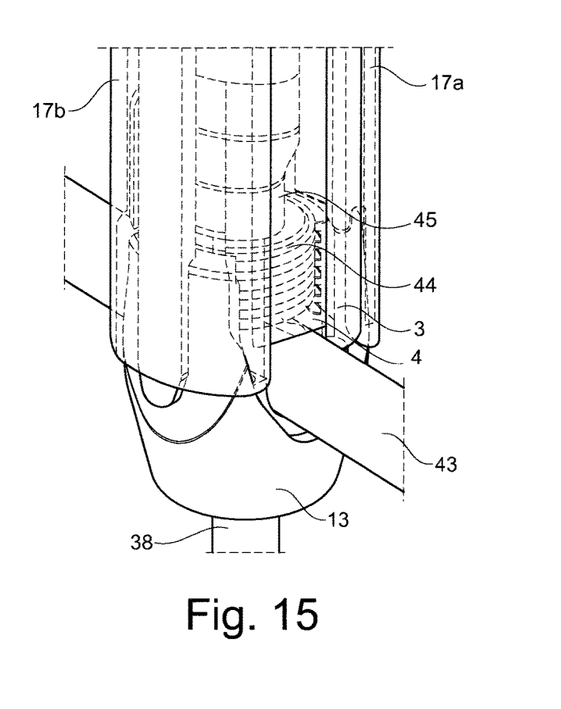
FIG. 15 is an enlarged truncated perspective view of the instrument and the pedicle screw of FIGS. 5 and 6 showing the process of screwing a set screw into the holding sleeve.

FIG. 15 shows the process of screwing in a set screw 44 as locking element 44 using the screw-driving tool 45. Together with the screw-driving tool 45 and the rod pusher 4, the set screw 44 can be guided through the pressure tappet 3 to the holding sleeve 13 and screwed into its internal thread. This causes the rod to be pressed into the holding sleeve 13 and the polyaxiality of the pedicle screw is blocked by the interaction of coupling unit 1, sleeve 2 and pressure tappet 3. In the first embodiment of the present invention with pressure tappet 3 and rod pusher 4, the screw-driving tool 45 is first passed through the rod pusher 4 and the set screw 44 is placed at the distal end of the latter. After this, the rod pusher 4 including the screw-driving tool 45 and the set screw 44 is guided through the provided opening of the pressure tappet 3 to the holding sleeve 13 and the set screw 44 is screwed into the internal thread of the holding sleeve 13.

In a first step, by screwing the pressure tappet 3 into the internal thread 7 of the coupling unit 1, a provisional fastening of the pedicle screw 14 can be achieved by dividing the pressure tappet 3 and the rod pusher 4, while the longitudinal beam 43 is still movable and adjustable. Only in a second step, the rod pusher 4 is screwed into the internal thread of the coupling unit 1, wherein the longitudinal beam 43 is pressed into the holding sleeve 13 to such an extent that the set screw 44 can be screwed into the holding sleeve 13. In a third step, the screw-driving tool 45 can now screw the set screw 44 into the internal thread of the holding sleeve 13 of the pedicle screw 14, whereby the polyaxiality is permanently blocked or fastened by the screw-in pressure of the set screw 44 acting on the rod 43, and further on the plunger and the shank head. After this, the provisional fastening of the medical instrument can be released and the medical instrument can be separated from the fastened pedicle screw 14 when decoupled.

Figure 17:
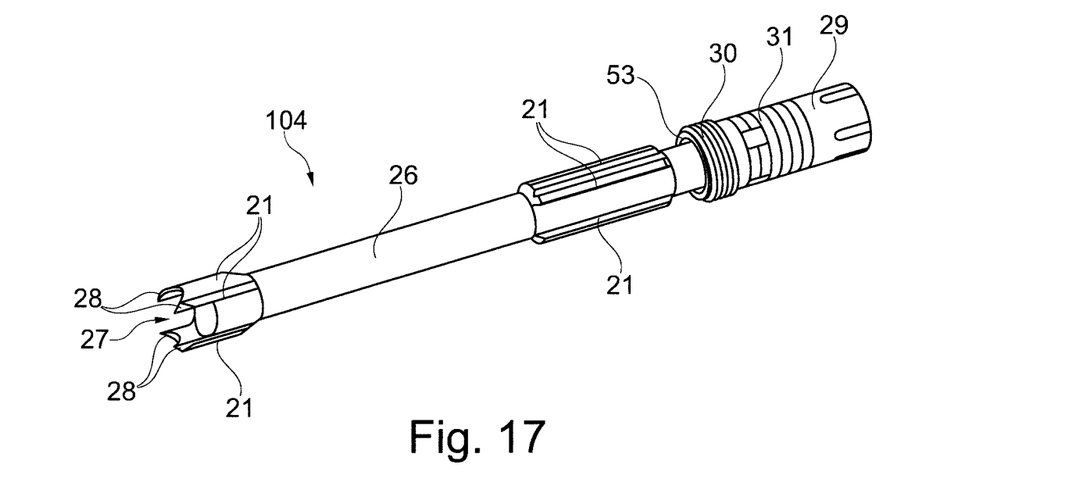
FIG. 17 is a perspective view of a pressing unit according to a second embodiment of an instrument according to the invention.

FIG. 17 shows a second embodiment of the present invention with a one-piece design of pressure tappet 3 and rod pusher 4 as the pressing unit 104. The pressing unit 104 comprises a substantially cylindrical rod 26, the distal end of which is designed as a rod mount 27 and has four support pins 28 projecting in the axial direction. The proximal end of the pressing unit 104 has a screw head 29 which is rotatable but coupled to the pressing unit 104 in an axially fixed manner, which is designed with an external thread 30 and carries a scale 31. As with the rod pusher 4, the external thread 30 is designed and formed for engagement with the internal thread 7 of the coupling element 1. By screwing or unscrewing the pressing unit 104 into or out of the coupling unit 1, as already in the rod pusher 4, their relative axial positioning and thus a corresponding axial positioning of the rod mount 27 relative to the coupling structure 10 is effected. In a central section and in the distal end region the pressing unit 104 is provided with four uniformly circumferentially spaced guide protrusions 21. These are designed and formed for guided interaction with the guiding grooves 20 of sleeve 2. The screw head 29 again has a knurled structure 53 on the distal underside.

Using the pressing unit 104, the surgeon can achieve both the fixation of the polyaxiality of the pedicle screw 14 and the rod pushing function of the longitudinal beam 43 in a single step due to the one-piece design.

Figure 18:
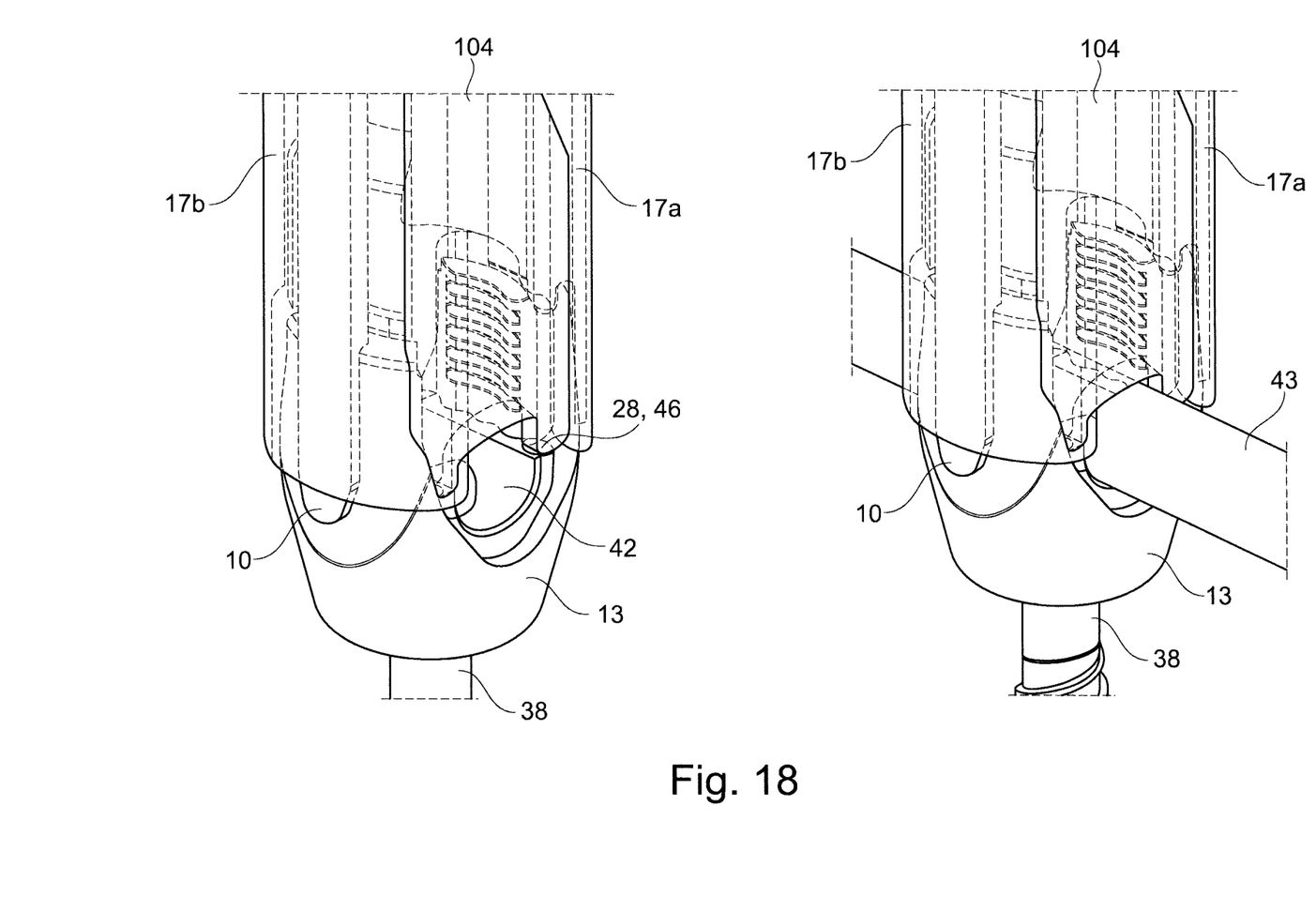
FIG. 18 is an enlarged truncated perspective view of the connection area of the instrument and the pedicle screw with inserted pressing unit with and without a longitudinal beam according to a second embodiment.

FIG. 18 shows the connection area between instrument and pedicle screw 14 with inserted pressing unit 104 of the second embodiment of the invention. Similar to FIG. 12 of the two-part design and its mode of operation, a clamping plunger 42 with four indentations 46 for the interaction with and the reception of the support pins 28 is again visible in the holding sleeve 13. By screwing the pressing unit 104 into the internal thread 7 of the coupling unit 1, a corresponding positioning relative to the sleeve 2 and to the coupling unit 1 and thus relative to the coupled holding sleeve 13 of the pedicle screw 14 takes place. This results in a tensioning of the clamping plunger 42 with respect to the holding sleeve 13, so that the shank head 39 is clamped between them and the polyaxiality of the pedicle screw 14 is fastened or blocked provisionally. FIG. 18 on the right shows a longitudinal beam 43 accommodated in the holding sleeve 13. Due to the one-piece design, the rod 43 is also pressed down into the holding sleeve 13 by screwing the pressing unit 104 into the internal thread 7, so that the set screw 44 can be screwed in.

Figure 19:
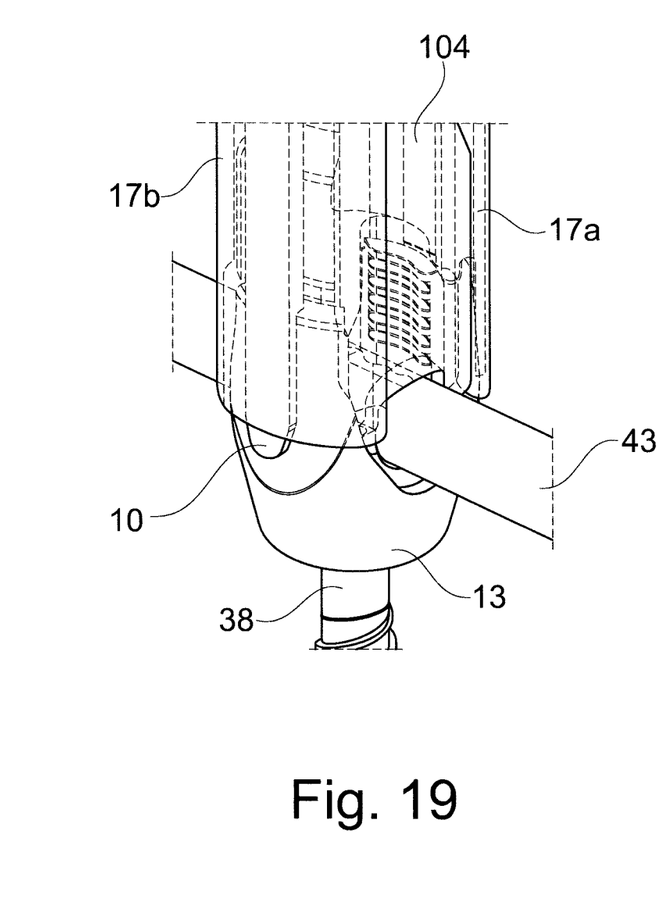
FIG. 19 is an enlarged truncated perspective view showing the process of pressing a longitudinal beam by means of the pressing unit into the holding sleeve according to the second embodiment.
Figure 20:
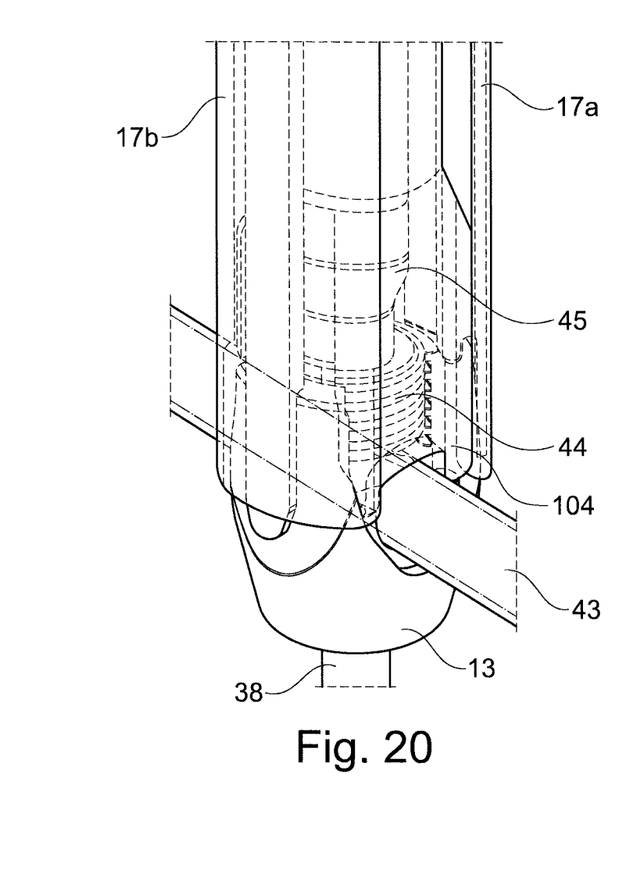
FIG. 20 is an enlarged truncated perspective view showing the process of screwing a set screw into the holding sleeve according to the second embodiment.

FIG. 19 shows the condition of the provisional fixation before screwing in a set screw 44. FIG. 20 shows, similar to the screwing process in FIG. 15, the screwing in of a set screw 44 as locking element 44 by means of the screw-driving tool 45. The set screw 44 together with the screw-driving tool 45 can be passed through the pressing unit 104 to the holding sleeve 13 and screwed into its internal thread.

The invention claimed is:

1. A medical instrument for provisionally fastening a polyaxial pedicle screw having a threaded shank having a shank head formed proximally thereon, on which shank head a holding sleeve is rotatably and/or pivotally arranged, a clamping plunger acting on the shank head being mounted in the holding sleeve, in such a way that the holding sleeve can be positionally fixed on the shank head by relative tensioning the holding sleeve and the clamping plunger, the instrument having a coupling unit for releasably engaging the holding sleeve and a pressure tappet for applying a pressing force to the clamping plunger in a distal direction, the coupling unit and the pressure tappet being movable relative to each other in an axial direction, wherein the medical instrument has a sleeve in which the coupling unit is arranged so as to be movable in the axial direction inside the sleeve such that the coupling unit can be coupled to or uncoupled from the holding sleeve in a first axial position and is non-detachably fastened to the holding sleeve in a second axial position in order to implement a provisional fastening of the polyaxial pedicle screw together with the pressure tappet by applying a tensile force to the holding sleeve by the coupling unit that is non-detachably fastened in the second axial position and by applying a pressing force by the pressure tappet to the clamping plunger thereby relative tensioning the holding sleeve and the clamping plunger.

2. The medical instrument according to claim 1, wherein the coupling unit has a radially inwardly projecting detent structure in a distal end region for coupling engagement with a mating detent structure of the holding sleeve provided therefor.

3. The medical instrument according to claim 2, wherein the detent structure is configured to be positioned relative to the sleeve in the radial direction.

4. The medical instrument according to claim 3, wherein in the second axial position the distal end region of the coupling unit bears against the sleeve in the radial direction.

5. The medical instrument according to claim 3, wherein the detent structure can be positioned due to elastic deformation of the coupling unit in the radial direction.

6. The medical instrument according to claim 2, wherein the detent structure engages in a mating detent structure formed by the sleeve such that a tensile force is transmitted from the coupling unit to the sleeve.

7. The medical instrument according to claim 6, wherein the mating detent structure has at least one surface which extends at least partially in the horizontal direction and relative to which the detent structure can be arranged distally in order to transmit the tensile force in a form-fitting manner.

8. The medical instrument according to claim 6, wherein the mating detent structure has a bulbous shape in its distal end region and/or has two opposite indentations in the form of an undercut protruding in the circumferential direction.

9. The medical instrument according to claim 1, wherein the coupling unit has at least one coupling arm extending in the axial direction, the distal end region of which can be positioned in the radial direction due to elastic deformation in the radial direction.

10. The medical instrument according to claim 9, wherein the coupling unit has a radially inwardly projecting detent structure in a distal end region for coupling engagement with a mating detent structure of the holding sleeve provided therefor, and wherein the transition from the at least one coupling arm to the detent structure is formed such that a radially outer side of the detent structure projects radially outwards with respect to a radially outer side of the at least one coupling arm.

11. The medical instrument according to claim 1, wherein the coupling unit and the sleeve are in engagement with one another via a thread and are configured to be axially positioned by mutual rotation.

12. The medical instrument according to claim 1, wherein the sleeve has its distal end provided with a mount for a section of the holding sleeve in the form of a groove, a projection or an undercut, formed so as to extend in the circumferential direction.

13. The medical instrument according to claim 1, wherein the coupling unit is provided with a central passage in the axial direction, in which the pressure tappet is arranged so as to be axially positionable.

14. The medical instrument according to claim 1, wherein the pressure tappet has the proximal end provided with a cylindrical base which is freely rotatable about the axial direction of the pressure tappet, is coupled to the pressure tappet in an axially fixed manner and with which an axial positioning of pressure tappet and coupling unit relative to one another is achieved.

15. The medical instrument according to claim 1, further comprising a rod pusher for pressing a rod or longitudinal beam to be fastened in the holding sleeve of the polyaxial pedicle screw in the distal direction, the pressure tappet having a central passage in the axial direction in which the rod pusher can be axially positioned.

16. The medical instrument according to claim 15, wherein the rod pusher has a central passage in the axial direction for receiving, in a manner so as to be rotatable about the axial direction, a set screw and/or a screw-driving tool for screwing the polyaxial pedicle screw and/or for screwing the set screw.

17. The medical instrument according to claim 15, wherein the rod pusher has a central passage in the axial direction for receiving, in a manner so as to be rotatable about the axial direction, a set screw and/or a screw-driving tool for screwing the polyaxial pedicle screw and/or for screwing the set screw and that the rod pusher has the proximal end provided with a rotatable screw head which is coupled in an axially fixed manner and with which the axial positioning relative to the coupling unit is effected.

18. The medical instrument according to claim 1, further comprising a rod pusher for pressing down in the distal direction a rod or longitudinal beam to be fastened in the holding sleeve of the polyaxial pedicle screw, the pressure tappet and the rod pusher being formed as a one-piece pressing unit.

19. The medical instrument according to claim 18, wherein the rod pusher or the pressing unit has the proximal end provided with a rotatable screw head which is coupled in an axially fixed manner and with which the axial positioning relative to the coupling unit is effected.

20. The medical instrument according to claim 18, wherein the pressing unit has a central passage in the axial direction for receiving, in a manner so as to be rotatable about the axial direction, a set screw and/or a screw-driving tool for screwing the pedicle screw and/or for screwing the set screw.

21. The medical instrument according to claim 1, wherein the sleeve has a central passage in the axial direction which has a substantially oval or elliptical cross-sectional shape transverse to the axial direction for receiving, in a manner so as to be rotatable about the axial direction, an eccentric for expanding the sleeve and/or the coupling unit.

22. A medical instrument for provisionally fastening a polyaxial pedicle screw having a threaded shank having a shank head formed proximally thereon, on which shank head a holding sleeve is rotatably and/or pivotally arranged, a clamping plunger acting on the shank head being mounted in the holding sleeve, in such a way that the holding sleeve can be positionally fixed on the shank head by relative tensioning the holding sleeve and the clamping plunger, the instrument having a coupling unit for releasably engaging the holding sleeve and a pressure tappet for applying a pressing force to the clamping plunger in the distal direction, the coupling unit and the pressure tappet being movable relative to each other in an axial direction, wherein the instrument has a sleeve in which the coupling unit is arranged so as to be movable in the axial direction such that the coupling unit can be coupled to or uncoupled from the holding sleeve in a first axial position and is non-detachably fastened to the holding sleeve in a second axial position in order to implement a provisional fastening of the polyaxial pedicle screw with the pressure tappet,     wherein the coupling unit has a radially inwardly projecting detent structure in a distal end region for coupling engagement with a mating detent structure of the holding sleeve provided therefor,     wherein the coupling unit has at least one coupling arm extending in the axial direction, the distal end region of which can be positioned in a radial direction due to elastic deformation in the radial direction, and     wherein the transition from the at least one coupling arm to the detent structure is formed such that a radially outer side of the detent structure projects radially outwards with respect to a radially outer side of the at least one coupling arm.

23. The medical instrument according to claim 22, wherein the detent structure is configured to be positioned relative to the sleeve in the radial direction.

24. The medical instrument according to claim 23, wherein in the second axial position the distal end region of the coupling unit bears against the sleeve in the radial direction.

25. The medical instrument according to claim 22, wherein the sleeve has its distal end provided with a mount for a section of the holding sleeve in the form of a groove, a projection or an undercut, formed so as to extend in a circumferential direction.

\* \* \* \* \*